United States Patent [19]

Christmas et al.

[11] Patent Number: 4,474,015
[45] Date of Patent: Oct. 2, 1984

[54] METHOD OF AND APPARATUS FOR THE CONTROLLED COOLING OF A PRODUCT

[75] Inventors: Michael J. Christmas, Worcester Park; Brian M. Palmer, Farnborough, both of England

[73] Assignee: Planer Products Limited, Sunbury-on-Thames, England

[21] Appl. No.: 435,306

[22] Filed: Oct. 19, 1982

[51] Int. Cl.³ .............................................. F25B 21/02
[52] U.S. Cl. ........................................................ 62/3
[58] Field of Search ...................... 62/3, 467, 62, 328, 62/448

[56] References Cited

FOREIGN PATENT DOCUMENTS 978441 12/1964 United Kingdom ...................... 62/3
1023597 3/1966 United Kingdom ...................... 62/3

Primary Examiner—Lloyd L. King
Attorney, Agent, or Firm—Young & Thompson

[57] ABSTRACT

For the controlled cooling of specimens which are at least partially of liquid form, especially biological specimens, it is important that crystallization at the freezing point takes place locally, without supercooling, and preferably with absorption of the latent heat of fusion. At a temperature which is a predetermined amount above a given critical temperature for the specimen, e.g. its freezing point, a Peltier effect module is energized to effect supplementary cooling at a local area, for example one end of the specimen. The Peltier effect module and the specimen in its container supported in a sample holder are relatively movable. Preferably, the module is displaced, this being initiated by the insertion and removal of the sample holder, preferably by direct mechanical engagement.

9 Claims, 10 Drawing Figures

FIG. 5a.
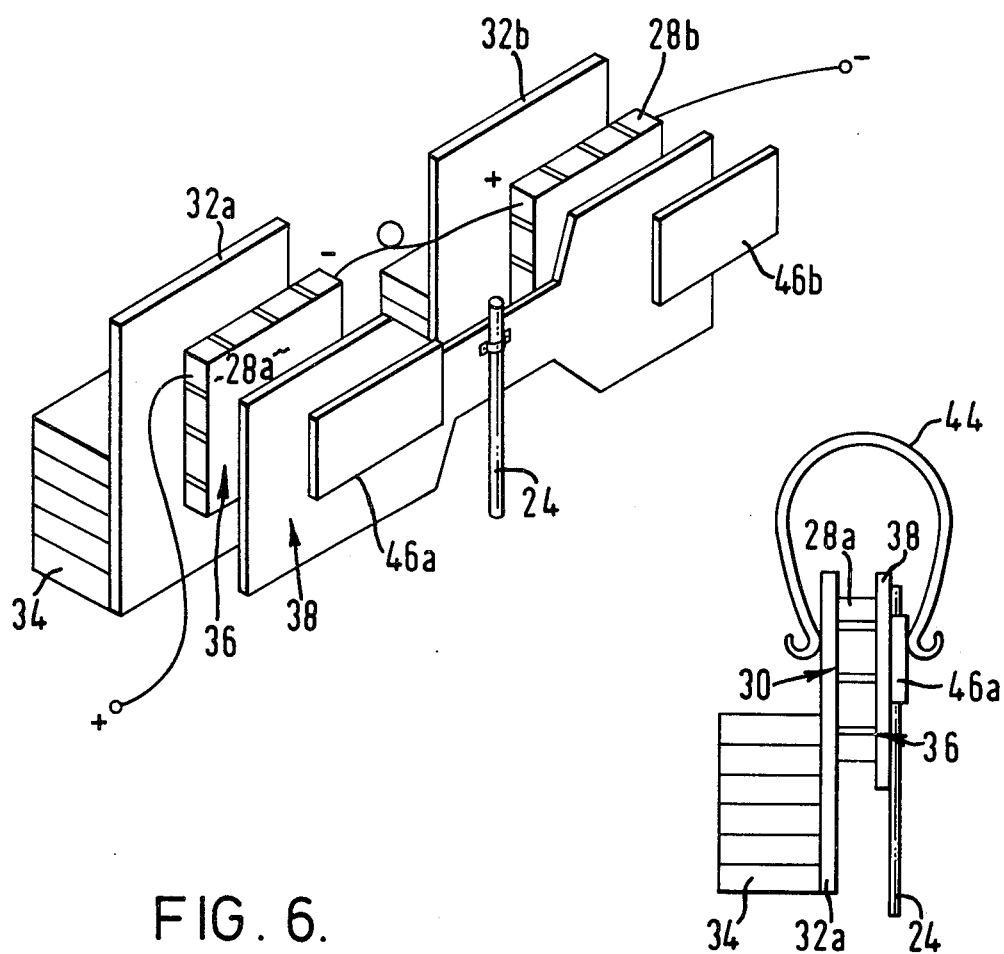
FIG. 5b.
FIG. 6.
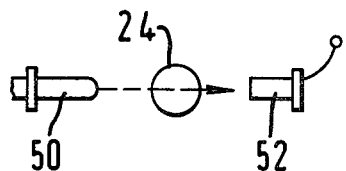

METHOD OF AND APPARATUS FOR THE CONTROLLED COOLING OF A PRODUCT

BACKGROUND OF THE INVENTION

This invention relates to methods of and apparatus for the controlled cooling of a product. The invention is particularly concerned with the controlled cooling of specimens which are at least partially in liquid form. One particular application of the invention is to the freezing, e.g. for preservation, of biological materials.

Reference is made to the co-pending U.S. Pat. application Ser. No. 435,308 in the name of M. J. Christmas filed on even date herewith and which describes and claims various features described hereinafter.

It is well known to freeze biological and other materials, e.g. animal embryos, blood constituents etc., for the purpose of preservation in carrier media. The material is frozen in a liquid carrier medium at an accurately controlled rate, for example by the release of liquid nitrogen or some other coolant which is evaporated in the vicinity of the specimen. Suitable control equipment is used in the admittance of the coolant to maintain the appropriate cooling rate. When biological material is cooled, the critical rate, for instance typically $-1°$ C. per minute is commenced above the freezing point of the solution/suspension. One difficulty encountered in such controlled freezing procedures, for example in the freezing of embryos in liquid nitrogen, results from the sudden crystallisation of constituents of the material to be frozen, for example at temperatures between $-7°$ C. and $-16°$ C. Experience has shown that without special precautions crystallization during cooling takes place effectively simultaneously throughout the body of the specimen, with the resulting "shock" causing damage to the biological material. For this reason it is common practice in such cases to induce crystallization at the upper end of the ampoule or other container for the specimen, by physically contacting the ampoule or container with tongs or some other metal member which has previously been cooled in liquid nitrogen. The local crystallization which is thereby initiated then spreads progressively downwards through the ampoule or container and throughout the body of the specimen. Because this crystallization is more progressive, the survival rate of the biological material is substantially enhanced.

Another problem encountered in such controlled freezing procedures, and this is not limited to biological specimens, is that when crystallisation occurs the latent heat of fusion of the solution/suspension is released and the temperature of the liquid rises. There is also the potential problem of supercooling of the liquid, again with the danger of instant massive crystallization throughout the body of the liquid.

Among the disadvantages of the known methods described above, particularly the use of metal tongs, is the necessity of introducing mechanical movement within the cooling chamber, or in some cases momentary withdrawal of the specimen container, thus creating a risk of upsetting the control of the cooling rate. In addition, such manoeuvres are extremely inconvenient to the operator and require skill and expertise in order to achieve consistent satisfactory results.

It is an object of the present invention to provide apparatus for modifying the cooling rate of a specimen which is at least partially in the liquid phase, in a controlled manner. This may be for example to induce crystallisation of the body of liquid at a particular location, or to induce precipitation or sedimentation of material from the liquid, or to absorb the heat of an exothermic reaction.

It is an object of a preferred embodiment of the present invention to provide an improved apparatus for at least partially removing the latent heat of crystallisation of a liquid which is progressively cooled, thereby considerably reducing the temperature rise within the liquid resulting from the latent heat of crystallisation.

Such preferred absorption of the latent heat of crystallisation or fusion is effected either automatically or under manual control without any need for mechanical movement of the specimen or the introduction of a foreign body, such as a pair of cold tongs.

In accordance with the present invention there is provided a cooling device for modifying the cooling rate of a specimen which is at least partially of liquid form, comprising cooling means arranged to be connected to an electric power source and to function in accordance with the Peltier effect to provide a surface at which heat is absorbed thereby to cool said surface, and a sample holder arranged to carry a specimen, wherein the cooling means and the sample holder are relatively movable to bring said surface of the cooling means into thermal contact with the specimen.

Preferably, there is provided means to displace said cooling means between a first position in which said surface is in thermal contact with said specimen and a second position in which said surface is remote from said specimen, wherein the displacement of said specimen into a position for cooling initiates the displacement of said cooling means from its said second position to its said first position.

Preferably the initiation of the displacement of said cooling means towards its said first position is effected by the sample holder striking against a portion of the cooling means.

Preferably said cooling means comprises a Peltier effect module mounted on a cantilevered support whereby the cooling means automatically moves to its said second position when the sample holder is removed.

In order that the invention may be fully understood various embodiments in accordance with the invention will now be described by way of example and with reference to the accompanying drawings, in which:

FIGS. 5a and 5b are similar perspective and side views of a second embodiment of cooling device in accordance with the invention;

FIG. 6 is a schematic illustration of an optical device which can be used in conjunction with the apparatus of the present invention.

The embodiments illustrated in FIGS. 1 to 6 are described also in the aforesaid co-pending U.S. patent application Ser. No. 435,308 in the name of M. J. Christmas entitled "Method of and apparatus for the controlled cooling of a product" filed on even date herewith.

Figure 1:
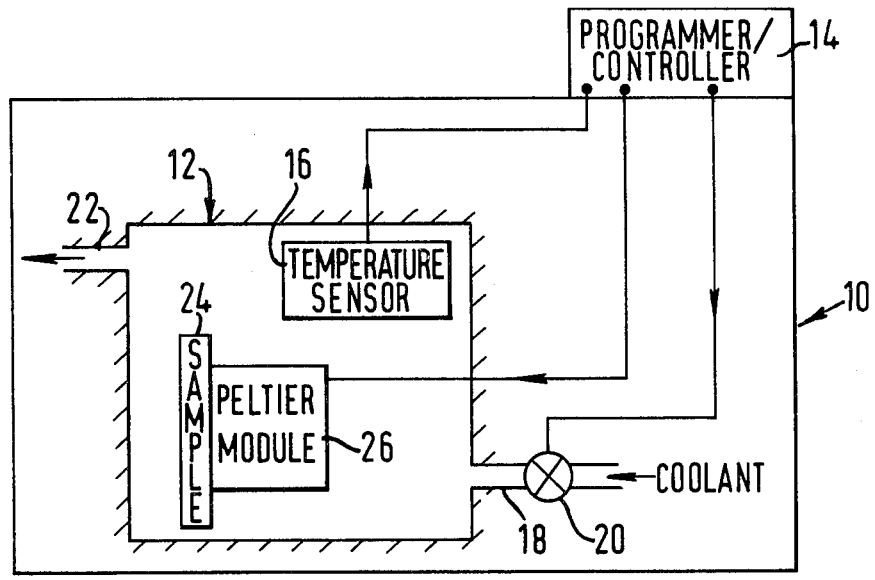
FIG. 1 is a schematic representation of a biological freezer incorporating a working chamber holding a specimen which is arranged to be cooled in a controlled manner in accordance with the present invention.

Referring first to FIG. 1, this shows a freezer 10, for example a conventional biological freezer, which incorporates a working chamber indicated generally at 12. Also provided is a programmer-controller unit 14 which is effective to control the temperature/time profile of the cooling process which takes place within the working chamber 12. For this purpose the programmer/controller unit 14 is connected to a temperature sensor 16, mounted within the working chamber. Connected to the working chamber 12 is a coolant supply pipe 18 which incorporates appropriate control valve means 20. This control valve means 20 is connected to the programmer/controller unit 14. An output pipe 22 is also connected to the working chamber 12. The freezer 10 is a conventional unit and the other component parts, mechanical, electrical and/or electronic, will not therefore be described in detail.

Within the working chamber 12 there is mounted a sample 24. This sample 24 contains the liquid or liquid and solid which is to be treated, for example frozen, and may comprise for example a glass ampoule, a bag or other container, a thick-walled plastics container, a plastics straw, or a metal container. It should be understood that the present invention is appropriate for use with a sample container of any shape or material.

Also mounted within the working chamber 12 is a unit, indicated generally at 26, which is at the heart of the present invention and which comprises a Peltier-effect type cooling device. Embodiments of such a device are shown in FIGS. 4, 5 and 7 and will be described in more detail later. The Peltier effect is the phenomenon whereby heat is absorbed, or liberated, at a junction where an electric current passes from one metal to another.

Figure 2:
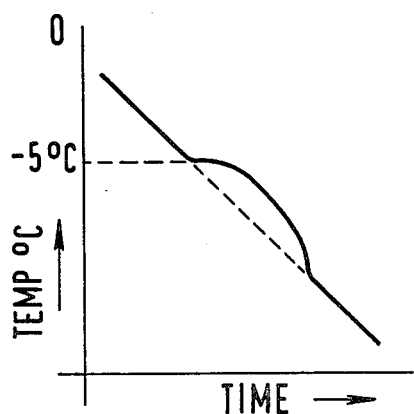
FIG. 2 is a graphical representation showing a typical rise in temperature which occurs in a liquid when it undergoes crystallization.
Figure 3:
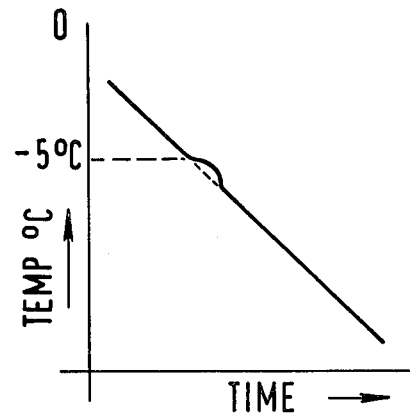
FIG. 3 is a similar graphical representation showing the effect of the use of the method and apparatus of the present invention in reducing the rise in temperature within the specimen.

FIG. 2 illustrates what happens when a liquid, for example a solution or suspension, is cooled through its freezing point. It will be seen that as the temperature falls from 0° C. to −5° C. the cooling curve is linear. At the freezing point, i.e. −5° C., as crystallization occurs, latent heat is generated which delays the further cooling of the liquid and creates an attendant risk of damage to biological specimens. The latent heat of crystallisation has to be absorbed by the gas around the sample 24 within the working chamber 12. In contrast, as shown in FIG. 3, with the method and apparatus of the present invention, one achieves a quite different rate of cooling curve. The curve departs only very slightly from the straight lines because of the much more rapid absorption of the latent heat with the system of the present invention. As will be explained hereinafter, the method and apparatus of the present invention provide local cooling for the sample, either to absorb this latent heat, instead of leaving this to the environmental gas within the chamber, or to initiate a boost in the cooling due to the environmental gas in the case where the local cooling is just used to induce crystal formation.

Figures 4A, 4B:
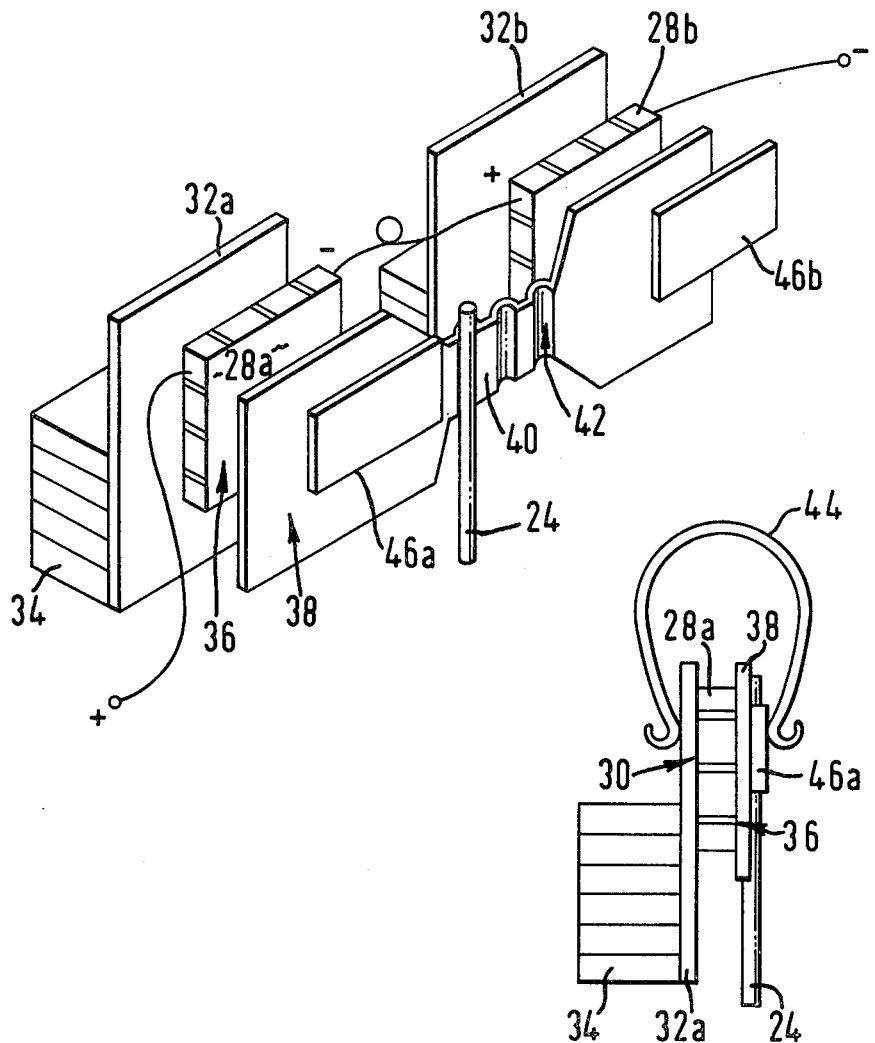
FIGS. 4a and 4b are perspective and side views respectively of a first embodiment of cooling apparatus in accordance with the present invention.

Referring now to FIGS. 4a and 4b, there is shown therein a first embodiment of the Peltier-effect type cooling device 26. Two Peltier-effect modules 28a and 28b are here connected in series to a suitable dc power supply source (not shown). Although a series electrical connection is shown, the modules could alternatively be connected in parallel or in some compound arrangement. Also, although in this described embodiment a pair of Peltier modules are used, one could alternatively use just a single such module. Each module comprises a series of p and n doped, bismuth telluride type limbs arranged in series so as to create a cold junction and a hot junction. The "hot" face 30 of each module 28a, 28b is covered with a suitable heat transfer compound, for example a grease, and a pair of heat sink plates 32a and 32b are secured respectively on the hot face of each module. Each of the heat sink plates 32a, 32b is equipped with fins 34 to enable the heat transferred to the heat sink plates to be dissipated into the working chamber 12 in such a way that the temperature/time profile set by the temperature programmer/controller unit 14 is maintained. The "cold" faces 36 of the Peltier-effect modules 28a, 28b are also covered with a suitable heat transfer compound, such as a grease, and a conductive metal strip or plate 38 is mounted so as to connect these two cold faces 36. As shown in FIG. 4a, the conductive metal strip 38, which may be for example of copper, aluminum or some similar high conductivity material has three separate areas. These consist of a pair of end plates in contiguous and overlapping relationship with the respective modules 28a and 28b, and a central bridging strip 40 of reduced width. This bridging strip 40 is provided with one or more corrugations or indentations 42 which are shaped to accommodate the sample container 24 with surface-to-surface contact. The provision of such corrugations 42 allows an increased surface area contact between the strip 40 and the container 24, and is particularly suitable for containers 24 having poor thermal conductivity, for example glass or thick-walled plastics containers. A spring clip or clamp 44 is provided across the device to clamp the container or containers 24 on to the conductive strip 40. The distance apart at which the Peltier modules 28a and 28b are set is determined by the dimensions required to accommodate the container or containers 24 on the strip 40. Two thermal insulating plates 46a and 46b are provided on the respective wing portions of the conductive strip 38 on the faces thereof which are opposite those faces which are in contact with the modules 28a and 28b. Although in the preferred embodiment the sample container 24 is in direct surface-to-surface contact with the conductive strip 38, 40, one could simply have the container spaced slightly from the strip or from a "cold" face, thereby maintaining thermal contact but not necessarily surface contact. Also of course, the sample container could be horizontal rather than vertical, and simply laid on the strip or "cold" face.

FIGS. 5a and 5b show a slightly modified arrangement in which the central bridging portion 40 of the conductive strip 38 is not indented or corrugated but is flat. This embodiment, where there is a reduced surface-to-surface contact between the sample container 24 and the bridging portion 40 of the strip 38, is suitable for containers 24 which have a low thermal mass, for example plastics straws or metal containers. It will be appreciated that other configurations of conductive strip can be devised to match the requirements of particular shapes of container, and particular container materials.

FIG. 6 shows an optical device which can be used in conjunction with the controlled cooling device of the present invention to detect the phase change from the liquid state to the crystalline state. A light beam from a light source 50 is transmitted through the sample container 24 towards a receiver 52. When the sample within the container 24 is in the liquid state the light beam will be detected by the receiver 52, but when there is a change to the crystalline state upon freezing, or upon the creation of a precipitate or sediment within the container, the light beam will be attenuated or completely blocked and the receiver 52 will detect this change. This detector can be linked up to the programmer/controller unit 14 so that the additional cooling introduced by the Peltier modules 26 is immobilised as soon as crystallization, precipitation or sedimentation has taken place. The term "light beam" used in relation to FIG. 6 is intended to include not only visible light but also other electromagnetic radiation which can be transmitted in the form of a beam. Again, other types of sensor than optical sensors could be used to detect the aforesaid phase change.

One preferred method of operation of the apparatus as hereinbefore described will now be given. The apparatus is set up with a specimen in a sample container 24 clamped to the conductive strip 38, 40. The Peltier assembly is mounted in the working chamber 12 of the freezer 10. A coolant, such as liquid nitrogen, is passed into the working chamber 12 through the inlet 18 to cause cooling of the specimen and container 24. Preferably, the sample container 24 is mounted so that one end of the container is in contact with the bridging portion 40 of the conductive strip, so that the local cooling effected by the strip is effected at one end of the container. Particularly when freezing biological specimens, it is desirable to initiate crystallization from one end of the container, preferably the upper end. Additionally, the Peltier assembly is spring-loaded within the cooling chamber to engage with the sample container 24 throughout the cooling process.

The degree of heat conduction between the sample container 24 and the strip 38, 40 is preferably first determined by initial experimentation, together with the measurement of the freezing point. Having thus determined the parameters of the particular system, the system can be set up for initiation of the local cooling by way of the Peltier device at preferably less than about 2° C. above the determined freezing point of the sample. The intention is to absorb heat locally around the upper surface of the liquid in the container 24 in order locally to induce seed crystals within the liquid. By matching the thermal masses of the cooling device and of the container 24 it is possible to achieve a carefully controlled initiation of these seed crystals. Preferably, the programmer/controller unit 14 (FIG. 1) is connected to the Peltier module 26 by a lead 54 and produces separate signal outputs at predetermined temperatures which are passed to the Peltier device 26 so that the Peltier device is actuated at a precise predetermined temperature.

When the temperature of the sample within the container 24 is close to the freezing point, an electric current is passed through the Peltier device, resulting in the cold faces 36 becoming colder and lowering the temperature of the conductive strip 38, 40. An electric current of for example 0.5 amps at 12 volts may in practice be passed through the Peltier modules when the specimen has reached the determined temperature just above the critical crystallisation, precipitation or sedimentation point. The current is maintained for a period of for example 10 seconds in order to produce the necessary local cooling which will induce crystallization, precipitation or sedimentation at that part of the container which is in surface-to-surface contact with the strip 40. This crystallization, precipitation or sedimentation will then spread progresssively through the whole of the specimen as the temperature continues to fall due to the continuing presence of the surrounding coolant, whether boosted or not.

If an optical device as shown in FIG. 6 is used, then this will detect the phase change from the liquid state to the crystalline state in that part of the sample container wherein local cooling is initiated, and can be used to trigger the programmer/controller unit 14, for example to effect termination of the additional cooling by way of the Peltier device as soon as the local crystallization, precipitation or sedimentation is detected.

It will be appreciated that no mechanical movement is required to initiate the local cooling of the sample, and there is no need for the operator to interfere with the sample container itself during the cooling process. With the use of a microprocessor-type control unit as the programmer/controller unit 14, it is possible to programme this in such a way as to operate the Peltier device at a given preset temperature.

It is also advantageous to provide for vibration of the specimen during the cooling process. This can be achieved by mounting the whole assembly 24, 26 on a suitable vibrator mounted either outside or within the working chamber 12. The vibration of the specimen within the container 24 during the cooling process reduces the chance of local supercooling of the sample. This also makes it easier to predict the crystallisation point.

Figures 7A, 7B:
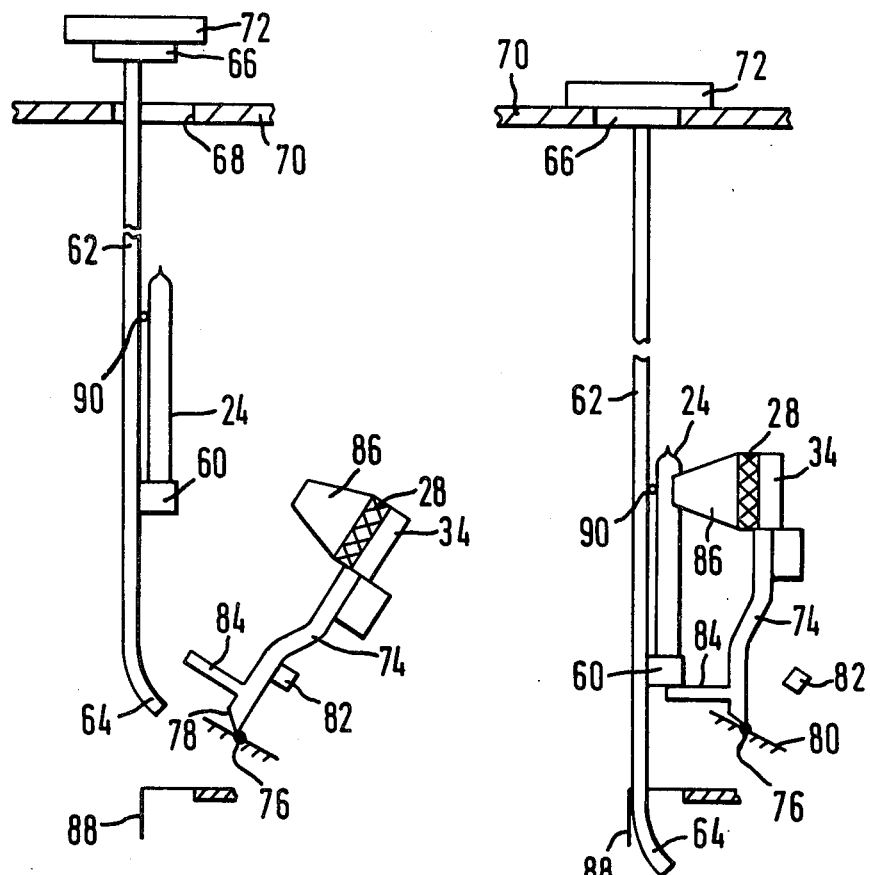
FIGS. 7a and 7b are side views of a further embodiment of cooling device in accordance with the invention.

In the embodiments of cooling device described above the sample containers 24 are either clipped to the Peltier modules or are held clamped against them, and the Peltier modules themselves are mounted in a fixed position. FIGS. 7a and 7b show an alternative embodiment of cooling device in accordance with the invention which is particularly useful for partial automation of the cooling cycles and procedures with which the present invention is particularly concerned. In this embodiment the Peltier module is not fixed, but is movable, and indeed movable in response to the presence or absence or a sample container. As will be explained in more detail, by the insertion of a sample container into the cooling device, the Peltier module is automatically brought into the current position for intimate contact with the sample container at the correct point in order to facilitate the desired shortterm supplementary cooling.

FIG. 7a shows the situation where a sample container in the form of an ampoule is about to be lowered into a working chamber which contains the Peltier module, and FIG. 7b shows the relative positions of the components after the ampoule has been lowered into the housing into thermal contact with the Peltier module.

As will be appreciated, in this embodiment, a single Peltier module is used, as compared with the use of a double module in the earlier embodiments. However, the device illustrated in FIGS. 7a and 7b is particularly appropriate for use when one has a working chamber adapted to receive a plurality of sample containers, and where one would then have a number of such Peltier modules mounted in rows or lines, or in some other array, within the working chamber, with each position receiving a respective one of the sample containers. One is thus able to effect the appropriate cooling of a number of samples under the same conditions and at the same time.

As shown in FIGS. 7a and 7b, the sample container 24, here shown as an ampoule, although it could be a straw or other container, is arranged to be carried in a bucket 60 secured to or integral with ampoule holder 62 in the form of an elongate rod having a curved lower end 64. The upper end of the ampoule holder 62 is provided with a cylindrical plug 66 sized to fit into a hole 68 through the top wall 70 of the working chamber, and with a cylindrical cap 72 by means of which the holder assembly can be grasped.

The Peltier module 28 is provided, as in the preceding embodiments, with cooling fins 34 and is mounted on a cranked support member 74. The support member 74 is pivotally mounted by a hinge member indicated at 76 and has a bottom surface 78 which, in the attitude shown in FIG. 7b, approaches a stationary stop 80. A further stop 82 is provided, against which the support member 74 rests when the assembly is in the position shown in FIG. 7a. A rod 84 which is secured to or is integral with the support member 74 projects forwardly from the support member and is arranged to extend horizontally when the assembly is in the position shown in FIG. 7b. The "cold" face of the Peltier module 28 has a yoke 86 fixed to it, for example by soldering. The yoke 86 is of a material which is an extremely good conductor of heat, and is preferably of copper. The yoke 86 is shaped so that it has a reducing cross-sectional area in the direction away from the face of the Peltier module, and the face of the yoke adjacent to the ampoule is suitably shaped so that it can make intimate contact with the ampoule. Thus, this face of the yoke is generally smoothly concave.

Below the Peltier module assembly there is mounted a stationary receptor 88 which has an upwardly directed hole or slot arranged to receive the ampoule holder 62 as it is lowered into the working chamber. The receptor 88 is positioned in relation to the ampoule holder 62 so that as the curved lower end 64 of the ampoule holder strikes the edge of the hole or slot in the receptor 88 the ampoule holder 62 will be "steered" so that the bucket 60 on the ampoule holder moves laterally towards the Peltier module assembly as the ampoule holder is lowered into the working chamber. A backing support 90 in the form of a rod is provided on the ampoule holder 62 at a position where it lies behind the ampoule 24.

In use, when the ampoule holder 62 is not present, or is in its raised position as shown in FIG. 7a, then the Peltier module assembly tilts backwards about the pivot 76, into contact with the stop 82, because of the cantilever effect arising from the Peltier module being mounted at the upper end of a cranked arm of the support member 74. When the ampoule holder 62, with an ampoule 24 having its base seated in the bucket 60, is lowered down through the hole 68 in the top of the working chamber, the curved lower portion 64 of the ampoule holder first strikes against the edge of the slot in the receptor 88, and the ampoule holder 62 is thereafter displaced so that the base of the bucket 60 strikes against the projecting rod 84 of the support member 74 and tilts the Peltier module assembly into an upright position, as shown in FIG. 7b. In this position the yoke 86 presses against the ampoule 24 at the desired position towards the upper end of the ampoule, and exerts a pressure against the ampoule against the restraining effect of the support rod 90.

With the components in the position shown in FIG. 7b one can then commence the cooling process in the manner already described above.

It will be appreciated that the cooling device as described in the latter embodiment is particularly attractive when one is considering semi-automation of the cooling of large numbers of samples. The ampoules or straws or other containers can be loaded into the ampoule holders outside the working chamber and, simply by lowering them into the working chamber, the Peltier module is brought accurately and reliably into contact with the appropriate part of the ampoule without manual adjustment and without the need for clips, springs, etc. It will be appreciated that the mechanical structure used for accomplishing this technique can be modified within the scope of the present invention. For example, instead of using an ampoule holder 62 having a curved lower end, one could use a straight rigid rod and provide a stationary inclined surface instead of the receptor 88, whereby the lower end of the rod, in striking against the sloping surface and sliding down it will again be displaced towards the Peltier module assembly in order that the bucket 60 would strike against the projecting rod 84.

A further advantage of the embodiment last described above is that the sample container, whether it be an ampoule, a straw or whatever, is reliably held in the correct position so that the right portion of the sample container is presented for contact by the yoke attached to the Peltier module itself.

Although the described embodiment shown in FIG. 7 uses direct mechanical engagement of the sample holder with the cooling assembly to initiate movement of the cooling assembly, one could alternatively use an electromechanical system where the insertion of the sample holder into the working chamber actuates a switch which triggers a motor to drive the cooling assembly from its out-of-contact position to its operational position.

It is emphasised that in its broadest aspect the present invention is concerned with affecting or modifying the rate of cooling of a specimen. The method and apparatus of the invention are therefore appropriate also for the absorption of the heat of an exothermic reaction occurring during a cooling process, even if no crystallisation, precipitation or sedimentation occurs at that point in the cooling process.

Additionally, although in the embodiment shown in FIGS. 7a and 7b the sample holder is movable in a generally straight path, here an essentially vertical path, and the cooling assembly is pivoted for pivotal movement, it should be understood that the present invention is not to be regarded as limited to this particular arrangement. Other ways of achieving relative movement between the cooling assembly and the sample holder are to be regarded as falling within the spirit and scope of the present invention.

We claim:

1. Cooling apparatus for modifying the cooling rate of a sample which is at least partially of liquid form, comprising means defining a working chamber, a sample holder adapted to carry a sample and insertable into and removable from said working chamber, locating means positioning the holder at a predetermined position in the chamber, cooling means within said working chamber adapted to be connected to an electric power source and to function in accordance with the Peltier effect to provide a surface at which heat is absorbed thereby to cool said surface, and means within the working chamber to effect movement of at least one of said cooling means and said sample holder in a direction to bring said surface of the cooling means into thermal contact with only a localized portion of the sample.

2. Cooling apparatus in accordance with claim 1, including pivot means on which the cooling means is pivotable toward and away from said sample, the sample holder being movable in a substantially straight path toward said predetermined position.

3. Cooling apparatus in accordance with claim 1, which includes means to displace said cooling means between a first position in which said surface is in thermal contact with said sample and a second position in which said surface is remote from said sample, and means responsive to movement of said sample into said predetermined position for localized cooling to initiate the displacement of said cooling means from its said second position to its said first position.

4. Cooling apparatus in accordance with claim 3, which includes an abutment surface on the cooling means, the initiation of the displacement of said cooling means toward its said first position being effected by the sample holder striking against said abutment surface.

5. Cooling apparatus in accordance with claim 3, which includes pivot means on which the cooling means is pivotable for displacement between its said first and second positions.

6. Cooling apparatus in accordance with claim 5, in which said cooling means comprises a Peltier effect module and cantilever support means on which the module is mounted, whereby the cooling means automatically moves to its said second position when the sample holder is removed.

7. Cooling apparatus in accordance with claim 1, in which the cooling means comprises a Peltier effect module and a heat-conductive element in contact with the module and defining said surface.

8. Cooling apparatus in accordance with claim 1, in which the sample holder comprises an elongated rod with carrier means thereon to support and locate a sample container, said carrier means being engageable with a projecting portion of said cooling means to initiate displacement of the latter.

9. Cooling apparatus in accordance with claim 1, which includes stationary abutment means within the working chamber, the sample holder comprising an elongated rod having a curved lower end which is slidingly engageable with said abutment means to steer the sample holder into a path in which it engages the cooling means to initiate displacement of the latter.

* * * * *